US012083736B2

(12) United States Patent
Backman et al.

(10) Patent No.: US 12,083,736 B2
(45) Date of Patent: Sep. 10, 2024

(54) TWO-PHASE 3D PRINTING METHODS OF FORMING BIOCOMPATIBLE STRUCTURES WITH IMMISCIBLE LIQUIDS

(71) Applicant: Lung Biotechnology PBC, Silver Spring, MD (US)

(72) Inventors: Daniel Backman, Bedford, NH (US); Mohammadali Safavieh, Nashua, NH (US); Aman Kaur, Manchester, NH (US); Derek Morris, Bedford, NH (US); Luis M. Alvarez, Lexington, MA (US)

(73) Assignee: Lung Biotechnology PBC, Silver Spring, MD (US)

( * ) Notice: Subject to any disclaimer, the term of this patent is extended or adjusted under 35 U.S.C. 154(b) by 0 days.

(21) Appl. No.: 17/971,168

(22) Filed: Oct. 21, 2022

(65) Prior Publication Data

US 2023/0131073 A1 Apr. 27, 2023

Related U.S. Application Data (60) Provisional application No. 63/271,670, filed on Oct. 25, 2021.

(51) Int. Cl.
*B29C 64/124* (2017.01)
*B29K 105/00* (2006.01)
(Continued)

(52) U.S. Cl.
CPC ............ *B29C 64/124* (2017.08); *B33Y 10/00* (2014.12); *B29K 2105/0061* (2013.01);
(Continued)

(58) Field of Classification Search
None
See application file for complete search history.

(56) References Cited

U.S. PATENT DOCUMENTS

2006/0022379 A1* 2/2006 Wicker ................. B33Y 70/00
264/401
2006/0237880 A1* 10/2006 Wicker ................. B33Y 30/00
264/401

(Continued)

FOREIGN PATENT DOCUMENTS

WO   WO-2017/210298 A1   12/2017
WO   WO-2018/182536 A1   10/2018
(Continued)

OTHER PUBLICATIONS

Calo et al., "Biomedical applications of hydrogels: A review of patents and commercial products," European Polymer Journal, Apr. 2015, 65:252-267.

(Continued)

*Primary Examiner* — Xiao S Zhao
*Assistant Examiner* — Guy F Mongelli
(74) *Attorney, Agent, or Firm* — Foley & Lardner LLP (57) ABSTRACT

A method of printing a hydrogel scaffold is provided which includes providing a container containing an ink and a liquid that is immiscible with the ink; applying light from a light source to the ink to form a portion of the hydrogel scaffold; and applying light from a light source one or more additional times to produce one or more additional portions of the hydrogel scaffold.

18 Claims, 10 Drawing Sheets

(51) Int. Cl.
*B33Y 10/00* (2015.01)
*B33Y 70/00* (2020.01)

(52) U.S. Cl.
CPC .......... *B29K 2105/0085* (2013.01); *B29K 2995/0093* (2013.01); *B33Y 70/00* (2014.12)

(56) References Cited

U.S. PATENT DOCUMENTS

| | | | |
|---|---|---|---|
| 2015/0165678 A1* | 6/2015 | Ding | B33Y 10/00 |
| | | | 425/150 |
| 2016/0046072 A1* | 2/2016 | Rolland | B29C 64/124 |
| | | | 264/401 |
| 2017/0217091 A1* | 8/2017 | Hull | B29C 64/40 |
| 2017/0239889 A1* | 8/2017 | Ganapathiappan | B33Y 10/00 |
| 2019/0009464 A1* | 1/2019 | Steege | B29C 64/336 |
| 2019/0022930 A1* | 1/2019 | Hinch | B29C 67/00 |
| 2019/0111613 A1* | 4/2019 | Morikawa | B29C 64/112 |
| 2021/0299951 A1* | 9/2021 | Lund | B29C 64/264 |
| 2022/0258410 A1* | 8/2022 | Ferre Romeu | B33Y 70/00 |
| 2022/0355541 A1* | 11/2022 | Melican | A61L 27/52 |

FOREIGN PATENT DOCUMENTS

| | | |
|---|---|---|
| WO | WO-2022/231521 A1 | 11/2022 |
| WO | WO-2022/236103 A1 | 11/2022 |

OTHER PUBLICATIONS

Beh et al., "A fluid-supported 3D hydrogel bioprinting method," Biomaterials, Sep. 1, 2021, 276:121034, 1-9.

\* cited by examiner

TWO-PHASE 3D PRINTING METHODS OF FORMING BIOCOMPATIBLE STRUCTURES WITH IMMISCIBLE LIQUIDS

CROSS-REFERENCE TO RELATED APPLICATIONS

This application claims priority to U.S. Provisional Application No. 63/271,670, filed Oct. 25, 2021, which is incorporated by reference in its entirety.

BACKGROUND

Compositions, including hydrogels, may be used to form objects used for biocompatible structures. These objects may be formed using three-dimensional (3D) printing techniques.

In traditional 3-D printing, a full container of ink is used even when printing large items. Reasons for this includes that the extra ink provides a buoyancy force that keeps the printed object from deforming and helps maintain attachment to the build platform. Additionally, the ink helps keep the printed hydrogel from dehydrating and shrinking, which can potentially cause build platform detachment. However, there are many drawbacks to using large quantities of ink. For instance, ink is expensive. Additionally, sourcing material for 3 L containers can have a long lead time between formulation development and large print.

Although in some cases ink can be reused, this too has drawbacks. Re-using ink may lead to unwanted variability. This variability may be difficult to quantify. Additionally, reusing ink increases the likelihood that a single batch of ink will need to be shared between multiple people and projects. Additionally, when reusing ink, often additional ink needs to be formulated and added to the reused ink to create the necessary print volume. This creates sub-optimal inter-dependencies. These interdependencies add complexity in planning projects It is against this background that a need arose to develop the embodiments described herein.

SUMMARY

To overcome this problem, certain embodiments of this specification use lower quantities of ink with a filler material. Benefits to this include the use of less ink and subsequent cost savings. Additionally, ink can be freshly made for each print. This can remove batch variability caused by the material print history (with variables including the number of prints, material age, source ingredient variability, and person making additional the ink). Additionally, formulation ingredients can be sourced in smaller of volumes.

An additional benefit is the ink does not need to be shared between different print runs, removing inter-dependencies. This reduces the time between new ink development and large print. Large prints can be made with almost any formulation and not just inks that can be reused. Additionally, one-off prints can be made at any time without concern of wasting residual ink. No long-term planning is required to consider how the reused material will be used. This may speed up model to print work cycle.

Embodiments disclosed herein include a process for printing large, hydrogel based objects such as hydrogel scaffolds with an inverted digital light projection (DLP) 3d printing system. During printing, the hydrogel object may be immersed in liquid during the entire print duration. In order to decrease the required ink, excess ink may be replaced with an alternate liquid. The alternate liquid may be immiscible with the ink. The alternate liquid may allow successful printing by providing buoyancy for the 3d printed scaffold and preventing dehydration during printing.

Embodiments of this disclosure relate to a method of printing a hydrogel scaffold. The method may include providing a container containing an ink and a liquid that is immiscible with the ink, applying light from a light source to the ink to form a portion of the hydrogel scaffold, and applying light from a light source one or more additional times to produce one or more additional portions of the hydrogel scaffold.

The hydrogel scaffold may remain immersed in the liquid that is immiscible with the ink during this method. In some embodiments, the liquid that is immiscible with the ink is selected from one or more hydrophobic substances. In some embodiments, the hydrophobic substance may include an oil with a viscosity of at least 5 cP or an organic solvent having a boiling point above 100° C. In some embodiments, the oil may have a viscosity of at least 10, 15, 20, or 50 cP. In some embodiment, the oil may have a boiling point above 120° C., 150° C., or 200° C. In some embodiments, the liquid that is immiscible with the ink is mineral oil, butyl acetate, mixture of butyl ether and mineral oil, petroleum ether (as well as liquids which have similar chemical properties of butyl either, butyl acetate, petroleum ether, or the density of the immiscible liquid is similar to those liquids) and mineral oil compositions in which the composition of petroleum ether is varying 25% (w/w)-50% (w/w). In some embodiments, the ink comprises a poly(ethylene glycol) di-(meth)acrylate monomer. In some embodiments, the poly(ethylene glycol) di-(meth)acrylate monomer has a weight average molecular weight ($M_w$) of about 400 to about 20,000. In some embodiments, the poly(ethylene glycol) di-(meth)acrylate monomer has a $M_w$ of about 2000 to about 7000.

In some embodiments, the ink comprises a photo initiator. The photo initiator may include lithium phenyl-2,4,6-trimethylbenzoylphosphinate (LAP), sodium phenyl-2,4,6-trimethylbenzoylphosphinate (NAP), Trimethylbenzoyl based photoinitiators, diphenyl(2,4,6-trimethylbenzoyl)phosphine oxide (TPO nanoparticle) Irgacure class of photoinitiators, ruthenium, and riboflavin, or mixtures thereof. The ink may include DI water. The ink may include about 50 to about 90% DI water. The ink may further include a protein, peptide, and/or extracellular matrices material.

Embodiments of this disclosure may relate to a method of reducing the amount of ink used during a digital light projection printing process to form a hydrogel scaffold. The method may include providing a container comprising a ink and a liquid that is immiscible with the ink; applying light from a light source to the ink to form a portion of the hydrogel scaffold; and applying light from a light source one or more additional times to produce one or more additional portions of the hydrogel scaffold, wherein the amount of ink used to form the hydrogel scaffold is at least 50% less than the amount of ink required to form the same hydrogel scaffold in the absence of the liquid that is immiscible with the ink.

The amount of ink used to form the hydrogel scaffold may be at least 50% less than the amount of ink required to form the same hydrogel scaffold in the absence of the liquid that is immiscible with the ink. The liquid that is immiscible with the ink may be selected from one or more hydrophobic substances. The one or more hydrophobic substances may include an oil with a viscosity of at least 5 cP or an organic solvent having a boiling point above 100° C. The liquid that is immiscible with the ink may be mineral oil, butyl acetate, mixture of butyl ether and mineral oil, Petroleum ether or a mineral oil composition. The composition of petroleum ether may vary between 25% (w/w)-50% (w/w).

The ink may include a poly(ethylene glycol) di-(meth)acrylate monomer. The poly(ethylene glycol) di-(meth)acrylate monomer may have a weight average molecular weight ($M_w$) of about 400 to about 20,000. The poly(ethylene glycol) di-(meth)acrylate monomer may have a $M_w$ of about 2000 to about 7000. The ink may include a photo initiator. The photo initiator may include lithium phenyl-2,4,6-trimethylbenzoylphosphinate (LAP), sodium phenyl-2,4,6-trimethylbenzoylphosphinate (NAP), trimethylbenzoyl based photoinitiators, diphenyl(2,4,6-trimethylbenzoyl)phosphine oxide (TPO nanoparticle) Irgacure class of photoinitiators, ruthenium, and riboflavin, or mixtures thereof. The ink may include DI water. The ink may include about 50 to about 90% DI water. The ink may include a protein, peptide, and/or extracellular matrices material.

Embodiments of this disclosure relate to the hydrogel scaffold formed by the methods disclosed.

BRIEF DESCRIPTION OF THE DRAWINGS

FIG. 4(A-E) shows an embodiment of two-phase printing of a model with a mineral oil second phase.

FIG. 5(A-B) shows an embodiment of two-phase printing of a Fischer bottle structure (5A is the digital model).

FIG. 6(A-C) shows an embodiment of two-phase printing of a small cube structure.

FIG. 7(A-B) shows an embodiment of two-phase printing of a formed lobe structure.

DETAILED DESCRIPTION

Definitions

As used herein, "3D printing" refers to any technique used to make a three-dimensional object using a digital model of that object by building layers using photopolymerizable ink.

As used herein, "printable ink" and "printable composition" refer to any composition that can be used to form an object using a 3D printing technique. A "ink" is a printable ink that forms a material with one or more desired mechanical, swelling, and/or biocompatibility properties. A bioink (also referred to as "bio ink" and " bio-ink") is a type of ink that include biological components, whether natural or synthetic, and/or is designed for biological compatability. The biological components may include peptides. An ink may contain one or more materials that facilitate adhesion and proliferation of desired cell types. The printed object may support primary cell and induced pluripotent stem cell attachment, proliferation, and spreading. In some cases, the ink can be formed into a hydrogel.

Process for Printing/Reducing Ink Usage

Disclosed here is a process for printing large, hydrogel based objects with an inverted digital light projection (DLP) 3d printing system, methods of reducing the amount of ink used during a digital light projection printing process, and hydrogel scaffolds formed by these processes. The hydrogel object may be composed of an ink. The ink may be water soluble and photocurable. The inks may contain components such as proteins, peptides, and extracellular matrices. Ink may evaporate during long print processes. It will be understood that "light" is used in a broad sense, and can include electromagnetic radiation capable of causing a polymeric reaction within the ink (either with or without a photo initiator).

During printing, the hydrogel object may be immersed in liquid during the entire print duration. This immersion may prevent dehydration and provide buoyancy. In order to keep the hydrogel immersed throughout the print duration, a large volume of ink is required. It may be a challenge to manufacture large quantities of ink in a cost-effective manner. The systems and methods for two-phase printing disclosed herein can provide as much as an 80% reduction in the amount of ink to successfully print large objects.

Accordingly, some embodiments include a method of printing a hydrogel scaffold the method comprising: providing a container comprising a ink and a liquid that is immiscible with the ink, applying light from a light source to the ink to form a portion of the hydrogel scaffold, and applying light from a light source one or more additional times to produce one or more additional portions of the hydrogel scaffold.

Also disclosed herein is a method for decreasing the required ink by replacing the excess ink with an alternate liquid. The alternate liquid may be immiscible with the ink. The alternate liquid may allow successful printing by providing buoyancy for the 3d printed scaffold and preventing dehydration during printing. In some embodiments, the liquid may be a hydrophobic liquid, such as an oil. In some embodiments, the liquid may be an alcohol. In some embodiments, the liquid may be an amphiphilic liquid.

Accordingly, some embodiments include method of reducing the amount of ink used during a digital light projection printing process to form a hydrogel scaffold, comprising; providing a container comprising a ink and a liquid that is immiscible with the ink, applying light from a light source to the ink to form a portion of the hydrogel scaffold, and applying light from a light source one or more additional times to produce one or more additional portions of the hydrogel scaffold, wherein the amount of ink used to form the hydrogel scaffold is at least 50% less (e.g., at least 50%, 55%, 60%, 65%, 70%, 75% less, or a range therein between) than the amount of ink required to form the same hydrogel scaffold in the absence of the liquid that is immiscible with the ink.

In some embodiments, the liquid that is immiscible with the ink is selected from one or more hydrophobic substance. For example, in some embodiments, the liquid that is immiscible is selected from mineral oil, butyl acetate, petroleum ether and mixtures thereof. In some embodiments, the mixture comprises about 25% (w/w) to about 50% (w/w) petroleum ether (e.g., about 25%, 30%, 35%, 40%, 45%, or 50% (w/w) petroleum ether). In some embodiments, the mixture comprises about 25% (w/w) to about 50% (w/w)

butyl acetate (e.g., about 25, 30, 35, 40, 45, or 50% (w/w) petroleum ether). In some embodiments, the mixture comprises mineral oil, e.g., about 50% (w/w) to about 90% (w/w) mineral oil (e.g., about 50%, 55%, 60%, 65%, 70%, 75%, 80%, 85%, or 90% (w/w), or a range therein between). In some embodiments, the one or more hydrophobic substances comprises an oil with a viscosity at 25° C. of at least 5 cP (e.g., at least 5, 6, 7, 8, 9, 10, 11, 12, 13, 14, 15, 20, 25 cP, or a range therein between) and/or an organic solvent having a boiling point at STP above 100° C. (e.g., above 105, 110, 120, 130, 140, 150, 160, 200, 250, 300, 350, 400, 450, 500, 550, 600, 650° C., or a range therein between)

The ink of the present embodiments is not particularly limited. In some embodiments, the ink comprises a poly (ethylene glycol) di-(meth)acrylate monomer. In some embodiments, the poly(ethylene glycol) di-(meth)acrylate monomer has a weight average molecular weight ($M_w$) of about 400 to about 20,000 (e.g., about 400, 500, 100, 1500, 2000, 2500, 3000, 3500, 4000, 4500, 5000, 5500, 6000, 6500, 7000, 7500, 8000, 8500, 9000, 9500, 10000, 10500, 11000, 11500, 12000, 12500, 13000, 13500, 14000, 14500, 15000, 15500, 16000, 16500, 17000, 17500, 18000, 18500, 19000, 19500 or 20000, or a range therein between).

In some embodiments, the ink comprises one or more of hydroxy $C_{1-2}$ alkyl (meth)acrylates, poly(alkylene oxide) alkyl ether (meth)acrylates, N-hydroxy $C_{1-2}$ alkyl (meth) acrylamides, a\ poly(ethylene glycol) methyl ether acrylate (PEGMEA), poly(ethylene glycol) methyl ether methacrylate, poly(propylene glycol) methyl ether acrylate, poly (propylene glycol) methyl ether methacrylate, hydroxyethyl acrylate (HEA), N-hydroxyethyl acrylamide (HEAA), hydroxyethyl methacrylate, hydroxypropyl acrylate (HPA 3-Hydroxypropyl acrylate and/or 2-Hydroxypropyl acrylate), hydroxypropylmethacrylate, hydroxybutyl acrylate (HBA), hydroxybutyl methacrylate, poly(alkylene oxide) di(meth)acrylates, diethylene glycol di(meth)acrylate, tetraethylene glycol di(meth)acrylate, N,N'-methylenebis(acylamide), (poly)lactic acid di(meth)acrylate, (poly)glycolic acid di(meth)acrylate, (poly)lactic-coglycolide di(meth) acrylate, (poly)caprolactone di(meth)acrylate, (poly)dioxanone di(meth)acrylate, (poly)fumarate di(meth)acrylate, (caboxy)(methyl)cellulose di(meth)acrylate, hyaluronic acid di(meth)acrylate, heparan sulfphate di(meth)acrylate, dextran di(meth)acrylate, alginate di(meth)acrylate, pectin di(meth)acrylate, tri-acrylates, or collagen di(meth)acrylate or mixtures thereof.

In some embodiments, the ink comprises further comprises a photo initiator. The photo initiator is not particularly limited, and any suitable photo initiator can be used. Examples of suitable photo initiators include lithium phenyl-2,4,6-trimethylbenzoylphosphinate (LAP), sodium phenyl-2,4,6-trimethylbenzoylphosphinate (NAP), Trimethylbenzoyl based photoinitiators, diphenyl(2,4,6-trimethylbenzoyl)phosphine oxide (TPO nanoparticle) Irgacure class of photoinitiators, ruthenium, and riboflavin, or mixtures thereof.

In some embodiments, the ink further comprises a solvent, such as water. In some embodiments the water is deionized. In certain embodiments, the ink comprises about 50 to about 90% DI water (e.g., about 50%, 55%, 60%, 65%, 70%, 75%, 80%, 85%, 90% DI water, or a range therein between).

In some embodiments, the ink further comprises a protein, peptide, and/or extracellular matrices material. In some embodiments the peptides are selected from the group consisting of RGD, KQAGDV, YIGSR, REDV, IKVAV, RNIAEIIKDI, KHIFSDDSSE, VPGIG, FHRRIKA, KRSR, APGL, VRN, AAAAAAAAA, GGLGPAGGK, GVPGI, LPETG(G)n, IEGR, and combinations thereof. Other examples of suitable additional components include ECM or ECM-like material such as amino acid sequence sensitive to a protease. The protease may be selected from Arg-C proteinase, Asp-N endopeptidase, BNPS-Skatole, Caspase 1-10, Chymotrypsin-high specificity (C-term to [FYW], not before P), Chymotrypsin-low specificity (C-term to [FYWML], not before P), Clostripain (Clostridiopeptidase B), CNBr, Enterokinase, Factor Xa, Formic acid, Glutamyl endopeptidase, GranzymeB, Hydroxylamine, Iodosobenzoic acid, LysC, Neutrophil elastase, NTCB (2-nitro-5-thiocyanobenzoic acid), Pepsin, Proline-endopeptidase, Proteinase K, Staphylococcal peptidase I, Thermolysin, Thrombin and Trypsin.

In some embodiments the hydrogel scaffold is similar shape and dimension as human organ. In some embodiments, the hydrogel scaffold remains immersed or submerged (or partially immersed) in the liquid that is immiscible with the ink during the method. In some embodiments, the hydrogel scaffold is submerged in the container. In some embodiments, the hydrogel scaffold is submerged in the container. In some embodiments, the method further comprising adding the liquid that is immiscible with the ink to replace at least a portion of the ink consumed or otherwise lost during the printing. In some embodiments, the liquid that is immiscible with the ink is positioned in the container to prevent the evaporation of the ink.

Printable Compositions (Hydrogel Scaffolds or Structures)

The printable compositions (hydrogel scaffolds or structures) described herein can be formed into three-dimensional objects that mimic or replicate an organ or a portion of an organ. For example, in some embodiments, the printable compositions described herein are formed into a structure that mimics or replicates the architecture of the lung, such as by using 3D printing techniques. The printable compositions can be used to form a scaffold for adhesion and growth of cells resulting in a structure that has one or more desired properties of an organ, such as a structure that can be perform the gas exchange functions of a lung. These objects can comprise a hydrogel. The organ or portion of an organ can be a human lung in a preferred embodiment.

In some embodiments, the 3D shape of the hydrogel structure is substantially the same shape, size, and/or has the same relative dimensions of an organ or a fragment of an organ. In certain embodiments, the organ or fragment of the organ comprises a vessel, trachea, bronchi, esophagus, ureter, renal tubule, bile duct, renal duct, bile duct, hepatic duct, nerve conduit, CSF shunt, lung, kidney, heart, liver, spleen, brain, gallbladder, stomach, pancreas, bladder, lymph vessel, skeletal bone, cartilage, skin, intestine, a muscle, larynx, or pharynx. In additional embodiments, the vessel shape comprises a pulmonary artery, renal artery, coronary artery, peripheral artery, pulmonary vein, or renal vein. In certain embodiments, the structure comprises a hemodialysis graft. Other embodiments include where the structure is substantially is the shape of a lung lobe, lung, airway tree of a lung, lung vasculature, or a combination thereof. In some embodiments, the reinforcement comprises maintaining air-flow or blood (or fluid) flow through the structure when an external pressure is applied to the structure.

The three-dimensional (3D) hydrogel structure is not particularly limited, and can be, e.g., a composite structure made of one or more different polymerized monomers.

Hydrogel materials that may be used in the invention may be known to those having ordinary skill in the art., as are methods of making the same. For example, a hydrogel as described in Caló et al., *European Polymer Journal Volume 65*, April 2015, Pages 252-267 may be used. In some embodiments, the hydrogel structure comprises a polymerized (meth)acrylate and/or (meth)acrylamide hydrogel. In some embodiments, the structure comprises a polymer comprising polymerized poly(ethylene glycol) di(meth)acrylate, polymerized poly(ethylene glycol) di(meth)acrylamide, polymerized poly(ethylene glycol) (meth)acrylate/(methacrylamide), poly(ethylene glycol)-block-poly(ε-caprolactone), polycaprolactone, polyvinyl alcohol, gelatin, methylcellulose, hydroxyethyl methyl cellulose, hydroxypropyl methyl cellulose, polyethylene oxide, polyacrylamides, polyacrylic acid, polymethacrylic acid, salts of polyacrylic acid, salts of polymethacrylic acid, poly(2-hydroxyethyl methacrylate), polylactic acid, polyglycolic acid, polyvinylalcohol, polyanhydrides such as poly(methacrylic) anhydride, poly(acrylic) anhydride, polysebasic anhydride, collagen, poly(hyaluronic acid), hyaluronic acid-containing polymers and copolymers, polypeptides, dextran, dextran sulfate, chitosan, chitin, agarose gels, fibrin gels, soy-derived hydrogels, alginate-based hydrogels, poly(sodium alginate), hydroxypropyl acrylate (HPA), lithium phenyl-2,4,6-trimethylbenzoylphosphinate (LAP) and combinations thereof. In some embodiments, the $M_w$ of the hydrogel polymer is about 400 Da, 500 Da, 600 Da, 700 Da, 800 Da, 900 Da, 1000 Da, 1100 Da, 1200 Da, 1300 Da, 1400 Da, 1500 Da, 1600 Da, 1700 Da, 1800 Da, 1900 Da, 2000 Da, 2100 Da, 2200 Da, 2300 Da, 2400 Da, 2500 Da, 2600 Da, 2700 Da, 2800 Da, 2900 Da, 3000 Da, 3100 Da, 3200 Da, 3300 Da, 3400 Da, 3500 Da, 3600 Da, 3700 Da, 3800 Da, 3900 Da, 4000 Da, 4100 Da, 4200 Da, 4300 Da, 4400 Da, 4500 Da, 4600 Da, 4700 Da, 4800 Da, 4900 Da, 5000 Da, 5100 Da, 5200 Da, 5300 Da, 5400 Da, 5500 Da, 5600 Da, 5700 Da, 5800 Da, 5900 Da, 6000 Da, 6100 Da, 6200 Da, 6300 Da, 6400 Da, 6500 Da, 7000 Da, 7500 Da, 8000 Da, 8500 Da, 9000 Da, 9500 Da, 10000 Da, 15000 Da, or 20000 Da.

In some embodiments, hydrogel comprises a cross linked polymer. In some embodiments, the polymer is about 0% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 100% cross-linked, based on the percentage of the cross-linkable moieties in the polymer. Cross linkable moieties may include, for example, (meth)acrylate groups.

The curable ink is not particularly limited. In some embodiments, the ink is the same or similar in composition to the monomers used in the three-dimensional (3D) hydrogel structure. In some embodiments, the curable ink is a photocurable ink, e.g., an ink that can be photocured in the UV spectrum range 100-400 nm. Possible inks include combinations containing a photoinitiator and/or dye that reacts and absorbs light at the range of 100-400 nm. Photoinitiators, may include, for example, benzophenone, phenyl bis (2,4,6-trimethylbenzoyl) phosphine oxide (BAPO), 2-hydroxy-2-methyl-1-phenyl-propan-1-one, 2-hydroxy-4'-(2-hydroxethoxy)-2-methylpropiophenone, 2,2'-azobis[2-methyl-n-(2- hydroxyethyl)propionamide], 2,2-dimethoxy-2-phenylacetophenone, diphenyl(2,4,6-trimethylbenzoyl) phosphine oxide, lithium phenyl(2,4,6-trimethylbenzoyl) phosphinate (LAP), sodium phenyl-2,4,6-trimethylbenzoylphosphinate (NAP), and ethyl (2,4,6-trimethylbenzoyl) phenylphosphinate.

An efficient technology among 3D printing technologies is a digital light process (DLP) method or stereolithography (SLA). In a 3D printer using the DLP or SLA method, the ink material is layered on a container or spread on a sheet, and a predetermined area or surface of the ink is exposed to ultraviolet-visible (UV/Vis) light that is controlled by a digital micro-mirror device or rotating mirror. In the DLP method, additional portions are repeatedly or continuously laid and each layer is cured until a desired 3D article is formed. The SLA method is different from the DLP method in that ink is solidified by a line of radiation beam. Other methods of 3D printing may be found in 3D Printing Techniques and Processes by Michael Degnan, December 2017, Cavendish Square Publishing, LLC, the disclosure of which is hereby incorporated by reference.

Figure 1:
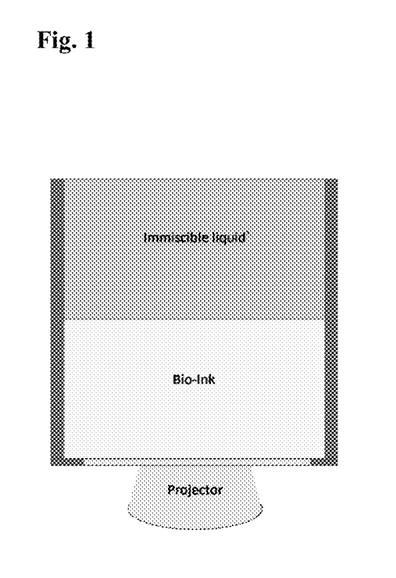
FIG. 1 shows an embodiment of two-phase print process setup with immiscible liquid in blue and ink in yellow
Figure 2A:
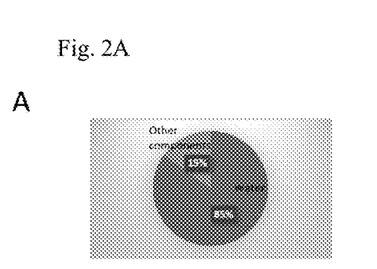
FIG. 2(a) shows an embodiment of a composition of the ink which has more than 85% DI water.
Figure 2B:
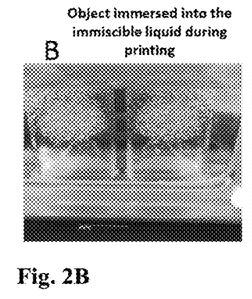
FIG. 2(b) shows an image of an embodiment of the printed object that is printed in mineral oil as a second phase.
Figure 2C:
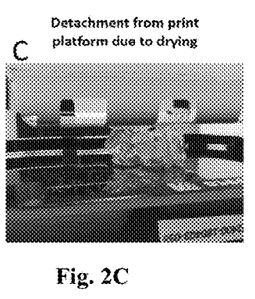
FIG. 2(c) shows an embodiment of a hydrogel that is printed outside of the ink, which resulted in failure.
Figure 2D:
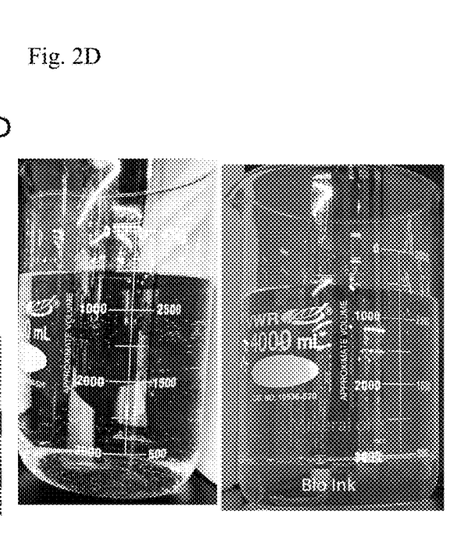
FIG. 2(d) shows the amount of the ink used in embodiments of one-phase and two-phase printing, showing a savings of more than 80% of the ink consumption.

During printing, the hydrogel object may be immersed in liquid during the entire print duration. This immersion may prevent dehydration and provide buoyancy. In order to keep the hydrogel immersed throughout the print duration, a large volume of ink is require. It may be a challenge to manufacture large quantities of ink in a cost-effective manner. The systems and methods for two-phase printing disclosed herein can provide as much as an 80% reduction in the amount of ink to successfully print large objects. FIG. 1 shows an embodiment phase print process setup with immiscible liquid in blue and ink in yellow.

FIG. 2 shows one embodiment of the disclosure. FIG. 2(*a*) shows the composition of one example of a ink. This ink comprises 85% Di water, making it immiscible with hydrophobic liquids such as mineral oil. FIG. 2(*b*) shows an image of the printed object which is printed in mineral oil as a second phase. In contrast, FIG. 2(*c*) shows a hydrogel that is printed outside of the ink, which resulted to failure. FIG. 2(*d*) shows the amount of the ink used in one phase and two phase printing, showing a savings of more than 80% of the ink consumption.

The following example describes specific aspects of some embodiments of this disclosure to illustrate and provide a description for those of ordinary skill in the art. The example should not be construed as limiting this disclosure, as the example merely provides specific methodology useful in understanding and practicing some embodiments of this disclosure.

Example 1

Figure 3:
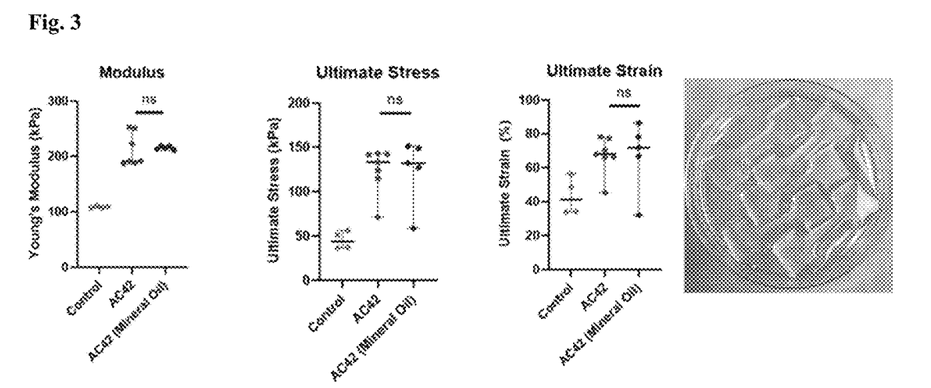
FIG. 3 shows mechanical properties modulus, stress, and strain of embodiments of a printed ink without collagen (controls), a printed ink with collagen (AC42), and a two-phase printed bioink with collagen and mineral oil (AC 42 Mineral oil).

FIG. 3 shows the mechanical properties of dogboned-shaped samples formed with one-phased or two-phase printing. The graphs show the modulus, stress, and strain for three different samples. The first sample shows printed ink without collagen (controls) using one-phase printing. The second sample shows printed ink with collagen (AC42) using a one-phase printing. The third sample shows ink with collagen using two-phase printing utilizing mineral oil for the second phase (AC 42 Mineral oil). Analysis of the tensile testing material property was completed between a sample that printed inside vat full of ink and ink that covered with mineral oil using printed dogbone structure. Uniaxial tensile testing was used to measure material properties such as Failure stress, failure strain and tensile modulus. The control sample was tested for certain printed properties including, certain exposure time and printer's power. The dogbone was printed with the dimensions as shown in FIG. 3. The dogbone was connected to Instron machine to measure tensile material properties. As can be seen from FIG. 3, the modulus, stress, and strain of dogbones formed using mineral oil and less ink had acceptable modulus, stress, and strain when compared with dogbones formed from a container of ink alone.

Example 2

FIG. 4: Ink was poured into the vat and mineral oil was added to the vat as shown in FIGS. 4A and B After the print is done the object transferred as shown in FIGS. 4C and D. An image of the printed object is shown in FIG. E.

Figure 4A:
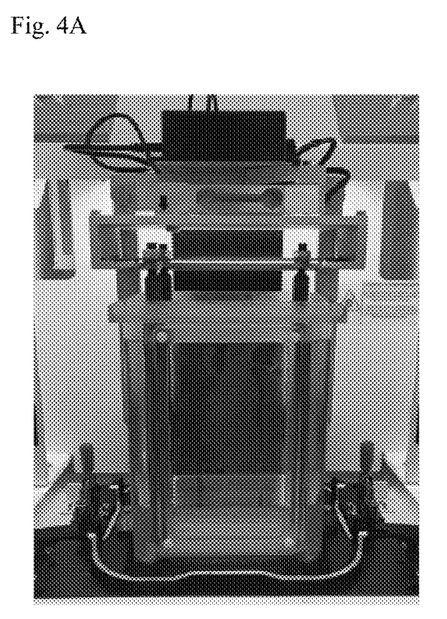
Figure 4B:
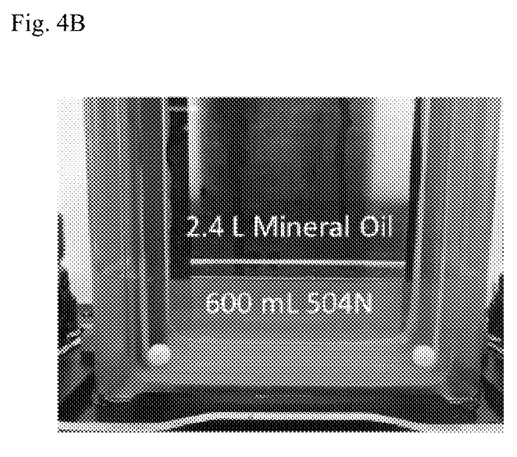

A digital light projection (DLP) 3d printing system was set up with a flat print platform. A ink comprising 600 ml of 504N with a PEGDA, LAP and UV386A™ (UV dye produced by QCR Solutions Corp.) was generated. FIG. 4A shows the 3-D printer setup. After the printer descended, 100 ml/min of mineral oil was added on top of the ink. FIG. 4B shows a close up of the interface between the ink and mineral oil.

Figure 4C:
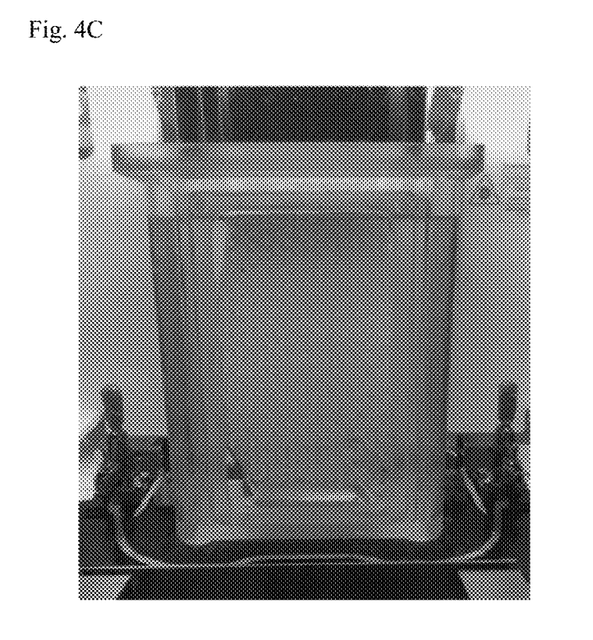
Figure 4D:
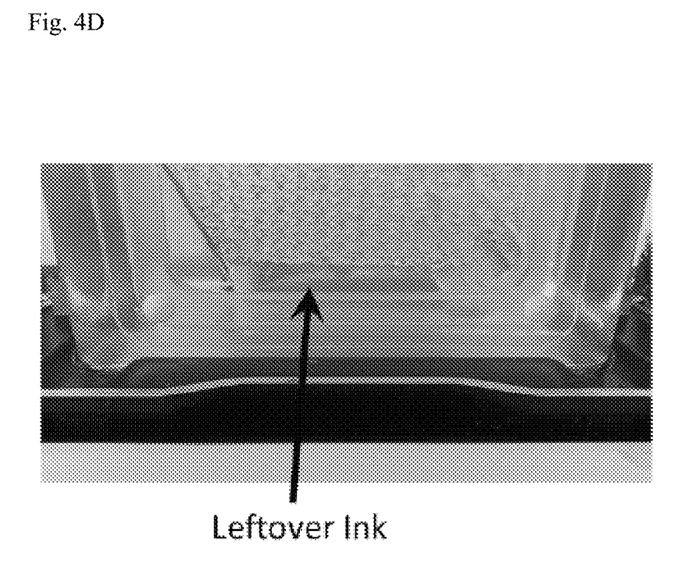
Figure 4E:
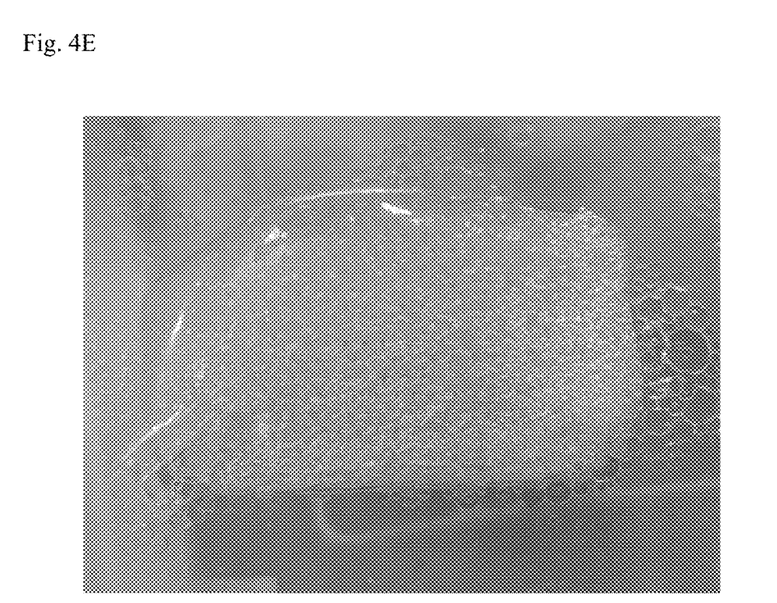

During the printing, a base of 10 portions was printing using a 35 sec print time per 100 μm layer. The body was printed at a rate of 7 seconds per 20 um layer. Photocuring was completed using a 200-400 Watt or 250-350 Watt or 275-325 Watt, such as 300 W, LED at 1.8-2.7 mW/cm$^2$ or 2.0-2.5 mW/cm$^2$ or 2.1-2.3 mW/cm$^2$, such as 2.22 mW/cm$^2$ As the model was printed, the printed model rose through the ink and into the mineral oil. FIG. 4C shows the successfully printed object formed from the 3-D printing ink. FIG. 4D is a close up of the small amount of left over ink after 3-D printing. FIG. 4E shows the finished object after 3-D printing coated in mineral oil.

Example 3

FIG. 5 shows a 3D printed ventilation Fischer bottle model printed using an ink comprising a PEGDA, LAP, and a UV dye. After the printer descended, 50 ml/min of mineral oil was added on top of the ink.

Figure 5A:
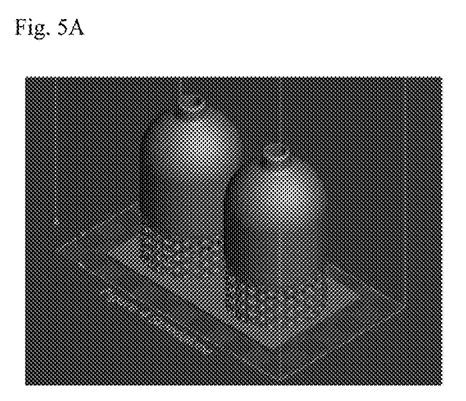
Figure 5B:
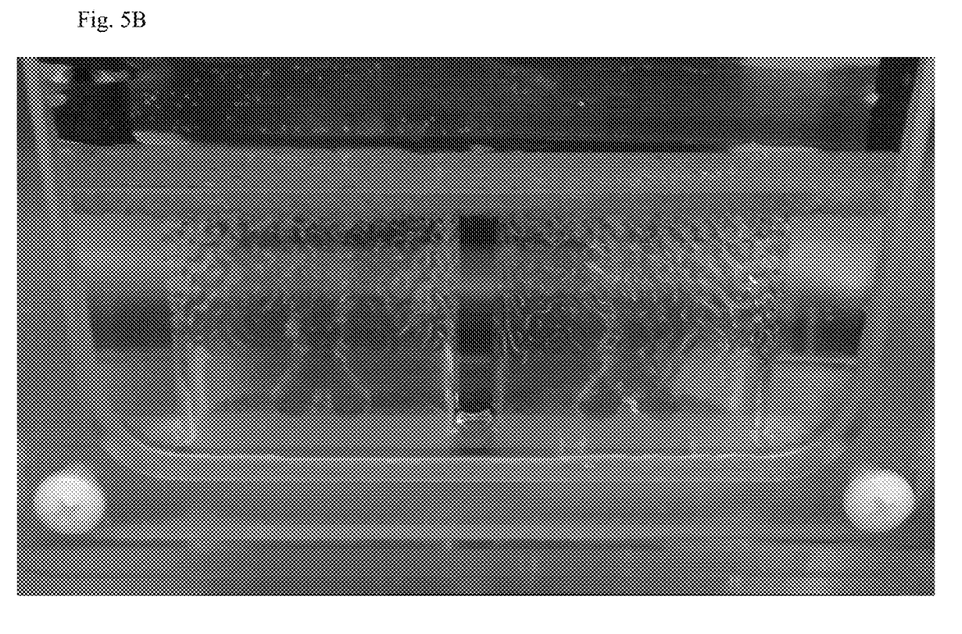

During the printing, a base of 10 portions was printing using a 25 sec print time per 100 μm layer The body was printed at a rate of 4 seconds per 50 um layer. Photocuring was completed using a 300-600 Watt or 350-550 Watt or 400-500 Watt or 425-475 Watt, such as 450 Watt LED at 2.5-4.5 mW/cm$^2$ or 3.0-4.0 mW/cm$^2$ or 3.25-3.75 mW/cm$^2$, such as 3.5 mW/cm$^2$ FIG. 5A shows a model of the Fischer bottle structure. FIG. 5B shows the Fischer bottle structure during printing in the large vat DLP printer in the two phases of ink and oil.

Example 4

Figure 6A:
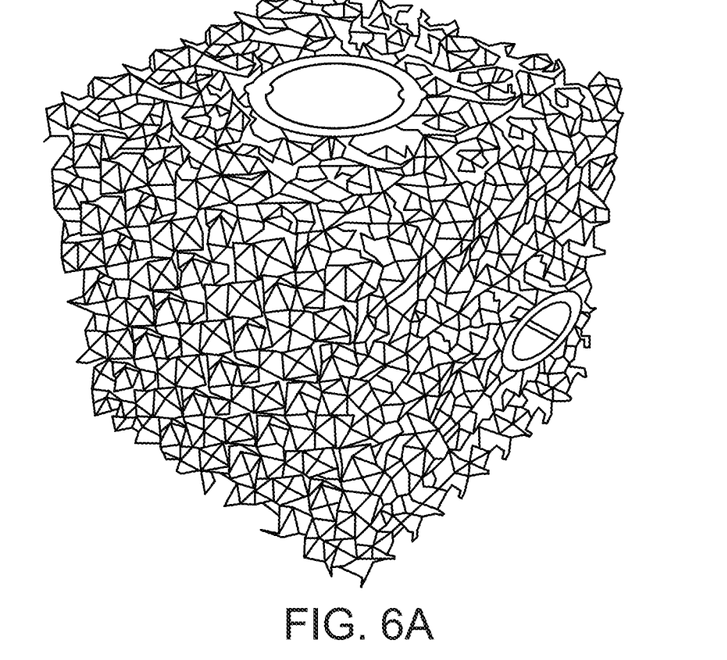

Example 4 shows printing a large hydrogel structure of a lobe-like model "objective 3". A cubic cutout of a G3-G4 juncture was modeled as shown in FIG. 6A. The diameter of the main inlets were around 400 um. The diameter of the main outlets were around 350 um. The diameter of the vascular net were around 200 um. The dimensions of the cute were around 3 cm cubed.

A DLP printer was used for 3D printing. In order to avoid undesirable reactions, a plastic build platform was used. Prior to 3D printing, a 300 nm thick titanium layer was sputtercoated onto a plastic build platform. The Titanium layer was coated with Silane.

Figure 6B:
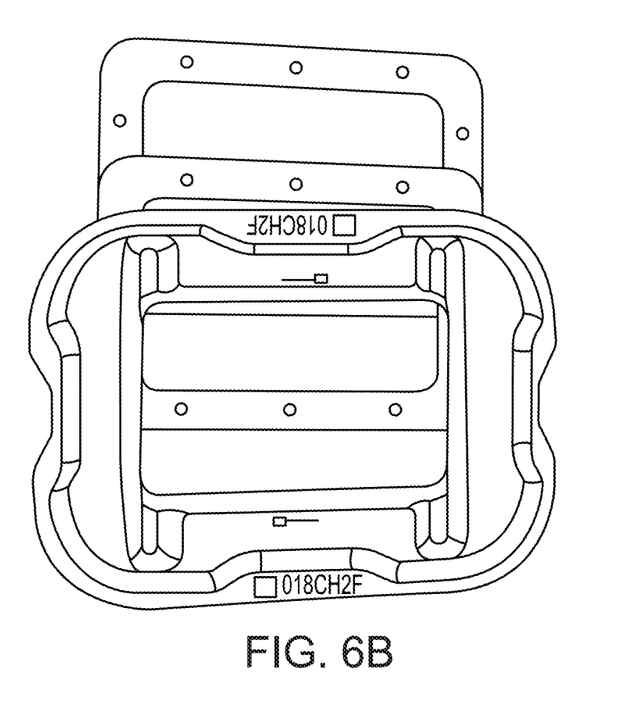

An ink was generated comprising a PEGDA, LAP and a UV dye. The ink was loaded into a container. The container shown in FIG. 6B was composed of black bath, blue gasket, AF2400 sheet (not shown), and chrome metal clamp. It was found that contact between the ink and the metal container resulted in coloration of the ink. To prevent contact between the dye and the metal container, a PDMS layer was added to the black surface of the container shown in FIG. 6B. The PDMS was prepared by mixing Sylgard 184 PDMS base with curing agent in a 10:1 ratio, speed mixing for 2 mins and then partially curing the mixture at 80 C for 30 min until the PDMS mixture was partially cured and more viscous. Approximately 30 grams of PDMS was applied to the black surface of the FIG. 4 Container. The container was cured at 80 C for 3-4 hours before used.

Figure 6C:
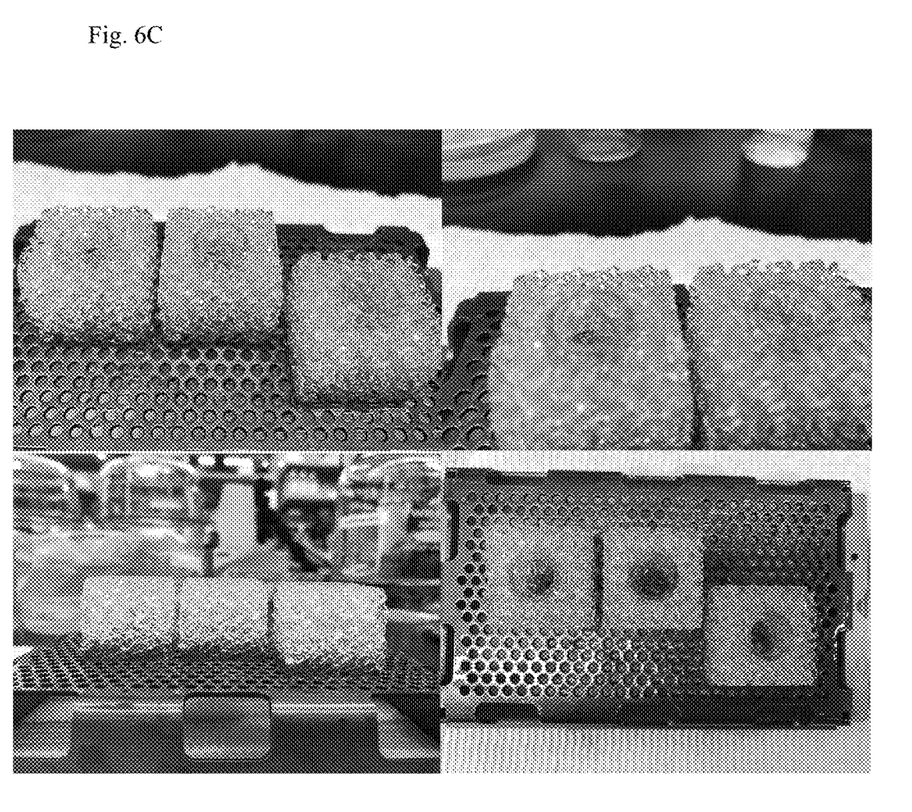

The cubes were 3-D printed using the DLP printer at 250 Watts with a build layer thickness of 20 um. In some embodiments, the ink formulation may be added to the container prior to printing and an immiscible liquid such as oil or alcohol may be added to cover the lobe as it is 3-D printed. Additional immiscible liquid may be added as needed to keep the lobe submerged. One example of the formed 3-D cubes are shown in the photograph of FIG. 6C.

A NextDent printer was used for 3D printing In order to avoid undesirable reactions, a plastic build platform was used. Prior to 3D printing, a 300 nm thick titanium layer was sputter coated onto a plastic build platform. The Titanium layer was coated with Silane methacrylate to improve adhesion of hydrogel to print platform.

An ink was generated from 503N combined with 1% LAP and 0.1% UV386A™ Dye (UV dye produced by QCR Solutions Corp.). The ink was loaded into a container. The Container shown in FIG. 6B was composed of black bath, blue gasket. AF2400 sheet (not shown), and chrome metal clamp. It was found that contact between the ink and the metal container resulted in coloration of the ink. To prevent contact between the dye and the metal container, a PDMS layer was added to the black surface of the container shown in FIG. 6B. The PDMS was prepared by mixing Sylgard 184 PDMS base with curing agent in a 10:1 ratio, speed mixing for 2 mins and then partially curing the mixture at 80 C for 30 min until the PDMS mixture was partially cured and more viscous. Approximately 30 grams of PDMS was applied to the black surface of the FIG. 4 Container. The container was cured at 80 C for 3-4 hours before used.

The lobe structure was 3-D printed using the DLP printer at 250 Irradiation mW with a build layer thickness of 20 um. [Please confirm the above is also accurate for the lobe structure as well as the cube structures.]

In some embodiments, the ink formulation may be added to the container prior to printing and an immiscible liquid such as oil or alcohol may be added to cover the lobe as it is 3-D printed. Additional immiscible liquid may be added as needed to keep the lobe submerged. One example of the formed 3-D cubes are shown in the photograph of FIG. 6C.

Figure 7A:
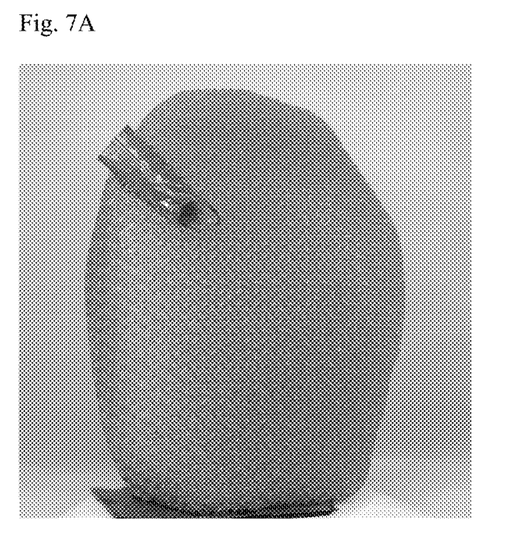
Figure 7B:
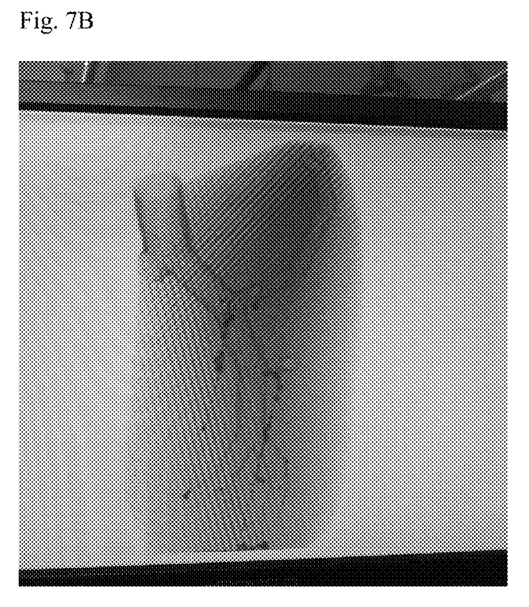

A microCt image was taken of the formed lobe structure, as shown in FIG. 7B.

As used herein, the singular terms "a," "an," and "the" may include plural referents unless the context clearly dictates otherwise. Thus, for example, reference to an object may include multiple objects unless the context clearly dictates otherwise.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. When referring to a first numerical value as "substantially" or "about" the same as a second numerical value, the terms can refer to the first numerical value being within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claim(s). In addition, many modifications may be made to adapt a particular situation, material, composition of matter method operation or operations to the objective spirit and scope of the disclosure. All such modifications are intended to be within the scope of the claim(s) appended hereto. In particular, certain methods may have been described with reference to particular operations performed in a particular order, it will be understood that these operations may be combined, sub-divided or re-ordered to form an equivalent method without departing from the teachings of the disclosure. Accordingly, unless specifically indicated herein, the order and grouping of the operations is not a limitation of the disclosure.

What is claimed is:

1. A method of printing a hydrogel scaffold comprising:
providing a container containing an ink and a liquid that is immiscible with the ink,
adding the liquid that is immiscible with the ink to replace at least a portion of the ink consumed or otherwise lost during the printing;
applying light from a light source to the ink to form a portion of the hydrogel scaffold; and
applying light from a light source one or more additional times to produce one or more additional portions of the hydrogel scaffold.

2. The method of claim 1, wherein the liquid that is immiscible with the ink comprises an oil with a viscosity of at least 5 cP or an organic solvent having a boiling point above 100° C.

3. The method of claim 1, wherein the liquid that is immiscible with the ink is selected from the group consisting of mineral oil, butyl acetate, a mixture of butyl ether and mineral oil, and a mixture of petroleum ether and mineral oil.

4. The method of claim 1, wherein the ink comprises poly(ethylene glycol) di-(meth)acrylate.

5. The method of claim 4, wherein the poly(ethylene glycol) di-(meth)acrylate has a weight average molecular weight ($M_w$) of about 400 to about 20,000.

6. The method of claim 4, wherein the ink further comprises at least one photoinitiator selected from the group consisting of lithium phenyl-2,4,6-trimethylbenzoylphosphinate (LAP), trimethylbenzoyl-based photoinitiators, diphenyl(2,4,6-trimethylbenzoyl)phosphine oxide (TPO nanoparticle) Irgacure class of photoinitiators, ruthenium, riboflavin, and mixtures thereof.

7. The method of claim 4, wherein the ink further comprises about 50% to about 90% DI water.

8. The method of claim 4, wherein the ink further comprises a protein, peptide, and/or extracellular matrices material.

9. The method of claim 1, wherein the hydrogel scaffold is at a human scale size.

10. The method of claim 1, wherein the printed portions of the hydrogel scaffold are immersed in the liquid that is immiscible with the ink during application of the light.

11. A hydrogel scaffold formed by the method of claim 1.

12. A method of reducing the amount of ink used during a digital light projection printing process to form a hydrogel scaffold, comprising:
providing a container comprising an ink and a liquid that is immiscible with the ink;
applying light from a light source to the ink to form a portion of the hydrogel scaffold; and
applying light from a light source one or more additional times to produce one or more additional portions of the hydrogel scaffold,
wherein the amount of ink used to form the hydrogel scaffold is at least 50% less than the amount of ink required to form the same hydrogel scaffold in the absence of the liquid that is immiscible with the ink and
wherein the liquid that is immiscible with the ink is a mixture of butyl ether and mineral oil that contains 25% (w/w)-50% (w/w) of petroleum ether.

13. The method of claim 12, wherein the hydrogel scaffold is submerged in the container.

14. The method of claim 13, wherein the hydrogel scaffold is entirely submerged by the ink or the liquid that is immiscible with the ink.

15. The method of claim 12, wherein the liquid that is immiscible with the ink is hydrophobic.

16. The method of claim 12, wherein the ink comprises poly(ethylene glycol) di-(meth)acrylate.

17. The method of claim 16, wherein the ink further comprises a photo initiator.

18. The method of claim 16, wherein the ink further comprises about 50% to about 90% DI water.

* * * * *